(12) United States Patent
Hadden et al.

(10) Patent No.: US 11,986,062 B2
(45) Date of Patent: May 21, 2024

(54) LEVER WEIGHTLIFTING BELT

(71) Applicants: General Leathercraft Manufacturing, Inc., Coleman, TX (US); Michael John Brunner, Coopersburg, PA (US)

(72) Inventors: Matthew Allen Hadden, Coleman, TX (US); Michael John Brunner, Coopersburg, PA (US)

(73) Assignee: General Leathercraft Manufacturing, Inc., Coleman, TX (US)

( * ) Notice: Subject to any disclaimer, the term of this patent is extended or adjusted under 35 U.S.C. 154(b) by 352 days.

(21) Appl. No.: 17/231,279

(22) Filed: Apr. 15, 2021

(65) Prior Publication Data

US 2021/0321725 A1 Oct. 21, 2021

Related U.S. Application Data

(60) Provisional application No. 63/013,010, filed on Apr. 21, 2020.

(51) Int. Cl.
*A44B 11/28* (2006.01)
*A41F 9/02* (2006.01)

(52) U.S. Cl.
CPC ............... *A44B 11/28* (2013.01); *A41F 9/02* (2013.01)

(58) Field of Classification Search
CPC ... A44B 11/28; A43C 11/1406; A43C 11/146; Y10T 24/2106; Y10T 24/2142; Y10T 24/2143; Y10T 24/216; Y10T 24/2183; Y10T 24/2187; A41F 9/02
See application file for complete search history.

(56) References Cited

U.S. PATENT DOCUMENTS

| | | | |
|---|---|---|---|
| 1,064,262 A | | 6/1913 | Utech |
| 3,132,392 A | * | 5/1964 | Sussman Steinberg ..................... A43C 11/1453 24/271 |
| 3,209,423 A | | 10/1965 | Jean-Victor |
| 4,051,611 A | | 10/1977 | Chalmers |
| 4,395,801 A | | 8/1983 | Gabrielli |
| 4,541,152 A | * | 9/1985 | DiMarco ............... A44B 11/125 24/271 |
| 4,674,156 A | * | 6/1987 | Olivieri .............. A43C 11/1453 24/71 SK |

(Continued)

FOREIGN PATENT DOCUMENTS

| | | | | |
|---|---|---|---|---|
| DE | 29704500 U1 | * | 4/1997 | ........... A43C 11/142 |
| DE | 29802825 U1 | * | 4/1998 | ........... A43C 11/142 |

*Primary Examiner* — Joshua T Kennedy
(74) *Attorney, Agent, or Firm* — Sheehan Phinney Bass & Green PA (57) ABSTRACT

A weightlifting belt includes a flexible strap portion with a first major surface (e.g., a front), a second major surface (e.g., a back), a first longitudinal end, a second longitudinal end, a first lateral side, and a second lateral side. An anchor assembly is in contact with the first major surface of the flexible strap portion near the first longitudinal end of the flexible strap portion. A lever-actuated hook assembly is in contact with the first major surface of the flexible strap portion near the second longitudinal end of the flexible strap portion. The lever-actuated hook assembly is configured to engage the anchor assembly so as to hold the first longitudinal end of the strap portion close to, or in physical contact with, the second longitudinal end of the strap portion so as to form a loop that can fit around a waist of a human.

24 Claims, 9 Drawing Sheets

(56) References Cited

U.S. PATENT DOCUMENTS

| | | | | |
|---|---|---|---|---|
| 5,630,253 | A * | 5/1997 | Benoit | A43C 11/1406 |
| | | | | 24/71 SK |
| 5,669,122 | A * | 9/1997 | Benoit | A43C 11/146 |
| | | | | 24/71 SK |
| 5,819,378 | A * | 10/1998 | Doyle | A43C 11/1406 |
| | | | | 24/71 SK |
| 9,339,083 | B2 * | 5/2016 | Benetti | A43C 11/144 |
| 9,526,966 | B2 * | 12/2016 | White | A44B 11/12 |
| 10,244,825 | B2 | 4/2019 | Greenham | |
| 2017/0245601 | A1 * | 8/2017 | Banks | A63B 71/12 |
| 2019/0374837 | A1 * | 12/2019 | Lamarque | A63B 71/00 |

\* cited by examiner

LEVER WEIGHTLIFTING BELT

CROSS-REFERENCE TO RELATED APPLICATION(S)

This application claims the benefit of priority to U.S. Provisional Patent Application No. 63/013,010 entitled ADJUSTABLE LEVER CLOSURE SYSTEM, which was filed on Apr. 21, 2020. The disclosure of the prior application is incorporated by reference herein in its entirety.

BACKGROUND

This disclosure relates to the field of weightlifting belts and, more particularly, relates to lever-style weightlifting belts.

Weightlifting belts are generally able to give weightlifters stability, support, etc. while lifting heavy weights.

SUMMARY OF THE INVENTION

In one aspect, a weightlifting belt includes a flexible strap portion with a first major surface (e.g., a front), a second major surface (e.g., a back), a first longitudinal end, a second longitudinal end, a first lateral side, and a second lateral side. An anchor assembly is in contact with the first major surface of the flexible strap portion near the first longitudinal end of the flexible strap portion. A lever-actuated hook assembly is in contact with the first major surface of the flexible strap portion near the second longitudinal end of the flexible strap portion. The lever-actuated hook assembly is configured to engage the anchor assembly so as to hold the first longitudinal end of the strap portion close to, or in physical contact with, the second longitudinal end of the strap portion so as to form a loop that can fit around a waist of a human.

In another aspect, a method is disclosed that includes placing a weightlifting belt around a waist of a person and fastening the weightlifting belt on the person's waist. The weightlifting belt includes a flexible strap portion that comprises a first major surface, a second major surface opposite the first major surface, a first longitudinal end, a second longitudinal end, a first lateral side, and a second lateral side. An anchor assembly is in contact with the first major surface of the flexible strap portion near the first longitudinal end of the flexible strap portion. A lever-actuated hook assembly is in contact with the first major surface of the flexible strap portion near the second longitudinal end of the flexible strap portion.

In some implementations, one or more of the following advantages are present.

For example, in some implementations, a weightlifting belt is provided that has lengthwise adjustability in ½ inch increments. The weightlifting belt can be used in multiple lifts without having to move the entire latch system. Also, the adjustable lever closure system can be retrofit to a variety of different belt designs.

Additionally, of course, in a typical implementation, the weightlifting belt with the adjustable lever closure system as described herein provides the usual advantages of support and stability while lifting heavy weights.

Moreover, in a typical implementation, the adjustable lever closure system disclosed herein makes it very easy, and comfortable, to put the weightlifting belt on and to take it off.

Additionally, in a typical implementation, the adjustable lever closure system disclosed herein allows the wearer the ability to adjust tightness on a belt it is worn on in several small (e.g., 0.5-inch increments) and allows the wearer the ability to have a 2-inch adjustable range (e.g., from the 0.5-inch increments) before having to move or adjust the support beam to a different position. Then, if further adjustment is needed (e.g., beyond the 2-inch adjustable range, the support beam can easily be moved too.

Other features and advantages will be apparent from the description and drawings, and from the claims.

BRIEF DESCRIPTION OF THE DRAWINGS

Like reference characters refer to like elements.

DETAILED DESCRIPTION

Figure 1A:
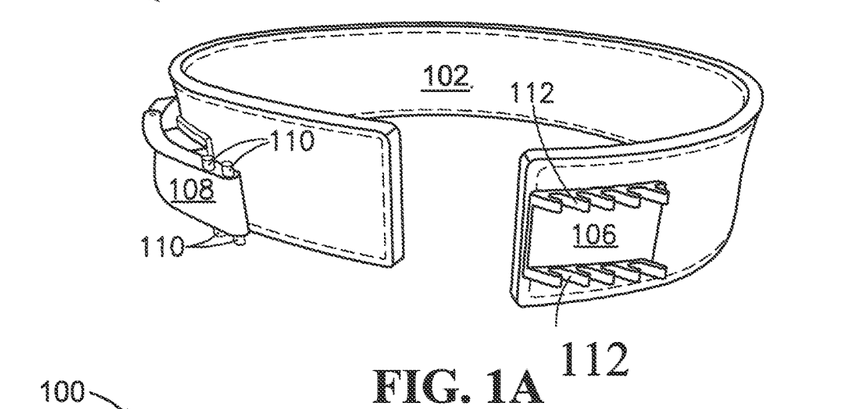
FIGS. 1A-1C are perspective views showing an exemplary implementation of a weightlifting belt.
Figure 1B:
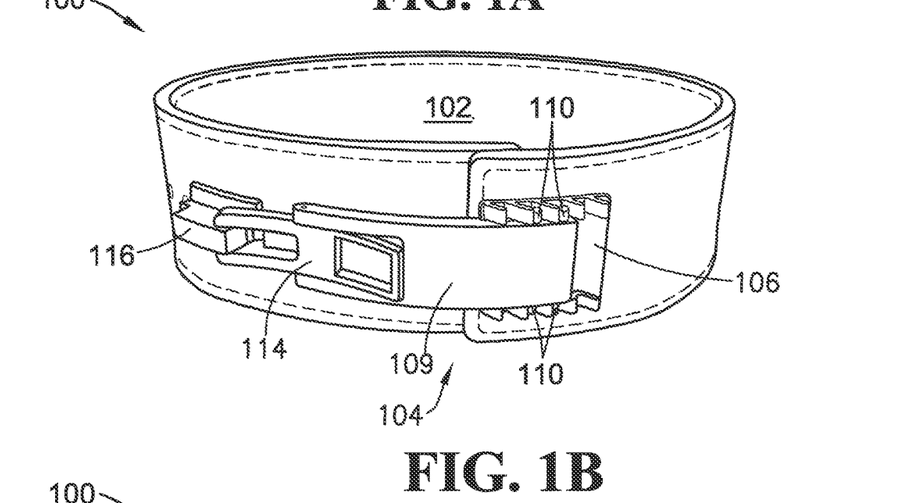
Figure 1C:
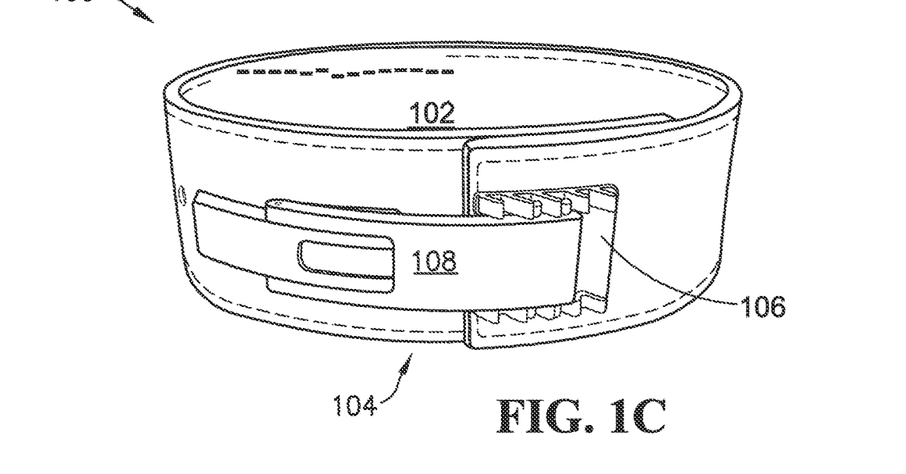

FIGS. 1A-1C are perspective views showing an exemplary implementation of a weightlifting belt 100. The weightlifting belt 100 has a flexible band or strap portion 102 and a fastening assembly 104 that can hold longitudinally opposite ends of the strap portion 102 close to one another so as to form a loop (e.g., around the waist of a wearer) with the strap portion. The fastening assembly 104 in the illustrated implementation has an anchor assembly 106 near one end of the strap portion 102, and a lever-actuated hook assembly 108 near the other end of the strap portion 102. The lever-actuated hook assembly 108 is configured to engage the anchor assembly 106 (to close the belt 100) and disengage the anchor assembly 106 (to open the belt 100).

FIG. 1A, for example, shows the weightlifting belt 100 in an open configuration. In this open configuration, the two ends of the strap portion 102 are separated from one another, and the fastening assembly 104 is open (i.e., the lever-actuated hook assembly 108 is not engaged with the anchor assembly 106). In this open configuration, a user is able to position the weightlifting belt 100 around his or her waist bringing the opposite ends of the strap portion 102 together. From that position, the user can extend the lever-actuated hook assembly 108 toward the anchor assembly 106 and engage the anchor assembly 106, as shown in FIG. 1B.

FIG. 1B shows the lever-actuated hook assembly 108 in an extended configuration and engaged to the anchor assembly 106. More specifically, the lever-actuated hook assembly 108 in the illustrated implementation has pins 110 that extend in a laterally-outward direction from a distal end of a hook portion 109 of the lever-actuated hook assembly 108. These pins 110 are configured to engage corresponding notches 112 in the anchor assembly 106. In this configuration, the strap portion 102 of the weightlifting belt 100 is substantially loop-shaped. Moreover, in this configuration, the strap portion 102 could extend around the waist of a person intending to wear and use the weightlifting belt 100. Typically, when the weightlifting belt 100 is in this configuration and around a person's waist, it will be relatively loose-fitting. Next, the user can operate the lever mechanism 114 of the lever-actuated hook assembly 108 to tighten the weightlifting belt 100 by pulling the anchor assembly 106 toward the end of the strap portion 102 where the lever actuated hook assembly 108 is mounted. Operating the lever mechanism of the lever actuated hook assembly 108 in this manner results in the weightlifting belt 100 being configured as shown in FIG. 1C.

FIG. 1C shows the belt in a closed and tightened configuration. The lever-actuated hook assembly 108 is in a retracted configuration and the anchor assembly 106 has been pulled toward the end of the strap portion 102 where the lever-actuated hook assembly 108 is mounted. In this configuration, the strap portion 102 of the weightlifting belt 100 is substantially loop-shaped. Moreover, in this configuration, the strap portion 102 could extend around the waist of a person with an appropriate degree of tightness, to provide the intended benefits of a weightlifting belt, around that person's waist.

From the configuration shown in FIG. 1C, the fastening assembly 104 can be very easily removed, for example, after the user completes a set of squats or other feat of strength. To do this, the user would simply operate the lever mechanism of the lever-actuated hook assembly 108 to loosen the fastening assembly 104. This would result in the weightlifting belt 100 reverting to the configuration shown in FIG. 1B where the lever-actuated hook assembly 108 is in an extended configuration, but still engaging the anchor assembly 106. As mentioned above, when the weightlifting belt 100 is in this configuration and around a person's waist, it will be relatively loose-fitting typically.

From the configuration shown in FIG. 1B, the weighting belt 100 can be opened for removal by simply disengaging the lever-actuated hook assembly 108 from the anchor assembly 106. This results in the weightlifting belt 100 returning to the open configuration in FIG. 1A.

There are at least two ways in which the illustrated weightlifting belt 100 can be adjusted to change its size (i.e., make it larger or smaller when in the closed and tightened configuration of FIG. 1C).

The first way to change the size of the weightlifting belt 100 would be to engage the pins 110 of the lever-actuated hook assembly 108 into a different set of notches 112 in the anchor assembly 106. For example, the pins 110 of the lever-actuated hook assembly 108 are engaged to a set of notches 112 in the anchor assembly 106 that make the size of the weightlifting belt 100, when closed and tightened relatively small. If, for example, the pins 110 of the lever-actuated hook assembly were engaged to a different set of notches (closer to the anchor assembly-end of the strap portion 102), then weightlifting belt 100 would be a larger size than it is in FIG. 1C.

The second way to change the size of the weightlifting belt 100 would be to change the mounting location of the lever-actuated hook assembly 110 on the strap portion 102. In this regard, the illustrated lever-actuated hook assembly 110 is securely fastened to the strap portion 102 of the weightlifting belt 100 via one or more fastening devices (e.g., bolts or the like, not shown in FIGS. 1A-1C). In a typical implementation, these fastening devices pass through one or more holes in the strap portion 102 of the weightlifting belt 100 to engage (and hold in place) the lever-actuated hook assembly 110. In a typical implementation, the strap portion 102 of the weightlifting belt 100 has a plurality of such holes, longitudinally-spaced relative to one another, that can accommodate the fastening devices. In such implementations, the mounting position of lever-actuated hook assembly 108 along the strap portion 102 of the weightlifting belt 100 can be adjusted by changing which mounting holes are used to mount the lever-actuated hook assembly 108. If, for example, the lever-actuated hook assembly 108 were mounted closer to its proximate end of the strap portion 102 of the weightlifting belt 100, then the weightlifting belt 100, when closed and tightened would be smaller than if the lever-actuated hook assembly 108 were mounted further from its proximate end of the strap portion 102 of the weightlifting belt 100.

In some implementations, yet another way to change the size of the weightlifting belt 100 would be to change the mounting location of the anchor assembly 106 on the strap portion 102. In this regard, the illustrated anchor assembly 106 is securely fastened to the strap portion 102 of the weightlifting belt 100 via one or more fastening devices (e.g., bolts or the like, not shown in FIGS. 1A-1C). In a typical implementation, these fastening devices pass through one or more holes in the strap portion 102 of the weightlifting belt 100 to engage (and hold in place) the anchor assembly 106. In some implementations, the strap portion 102 of the weightlifting belt 100 has a plurality of such holes, longitudinally-spaced relative to one another, that can accommodate the fastening devices. In such implementations, the mounting position of anchor assembly 106 along the strap portion 102 of the weightlifting belt 100 can be adjusted by changing which mounting holes are used to mount the anchor assembly 106. If, for example, the anchor assembly 106 were mounted closer to its proximate end of the strap portion 102 of the weightlifting belt 100, then the weightlifting belt 100, when closed and tightened would be smaller than if the anchor assembly 106 were mounted further from the end of the strap portion 102 of the weightlifting belt 100.

Thus, in a typical implementation, the fastening assembly 104 advantageously gives the user/wearer the ability to put the weightlifting belt 100 on and take the weightlifting belt 100 off easily and quickly. Moreover, the fastening assembly, in a typical implementation, gives the user/wearer the ability to adjust tightness of the weightlifting belt in small increments (e.g., 0.5 inch increments up to a maximum of about 2 inches) by changing which notches 112 the pins 110 engage, before having to move the mounting location of lever-actuated hook assembly 108 (or the anchor assembly 106). This ability to make small changes in tightness may be especially helpful to users/wearers who might gain or lose small amounts of weight from workout to workout.

Figure 2:
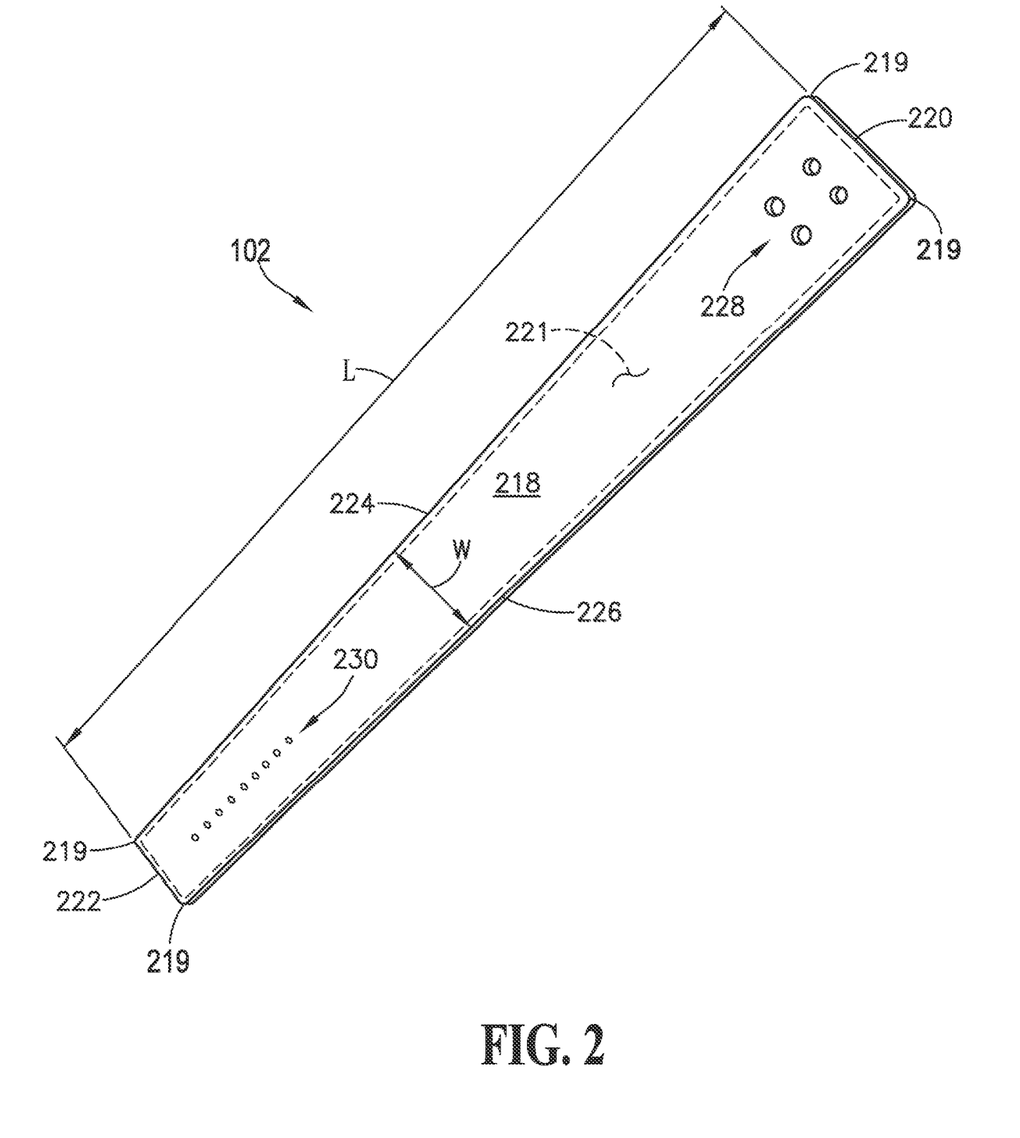
FIG. 2 is a view showing a first major surface (e.g., the back surface) of the strap portion of the weightlifting belt of FIG. 1.
Figures 3A, 3B, 3C, 3D:
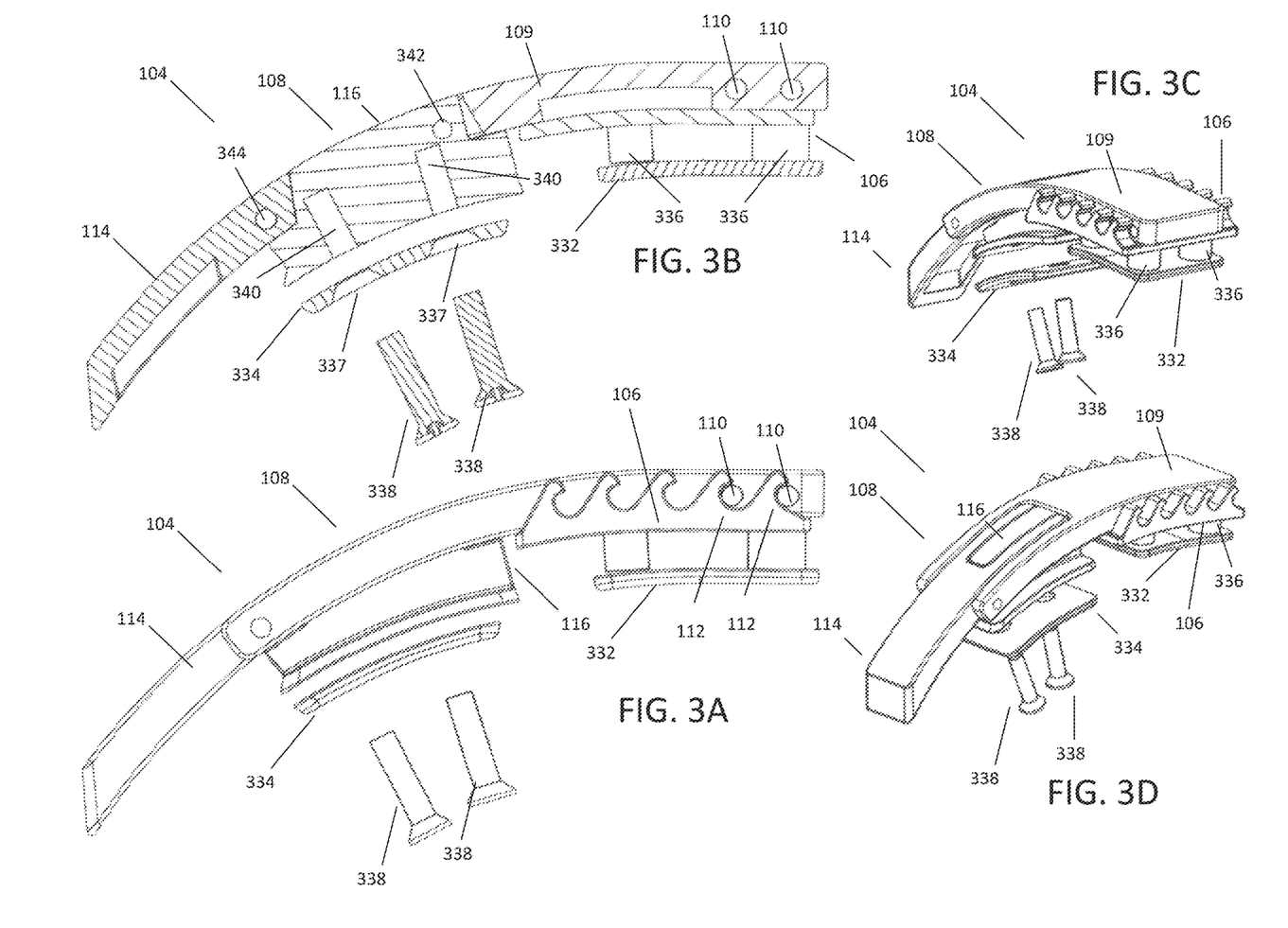
FIG. 3A is a side view showing component parts of the fastening assembly from FIG. 1A to 1C.
FIG. 3B is a cross-sectional side view showing the component parts of the fastening assembly from FIGS. 1A to 1C.
FIGS. 3C and 3D are perspective views showing the component parts of the fastening assembly from FIGS. 1A to 1C.
Figures 4A, 4B, 4C, 4D, 4E:
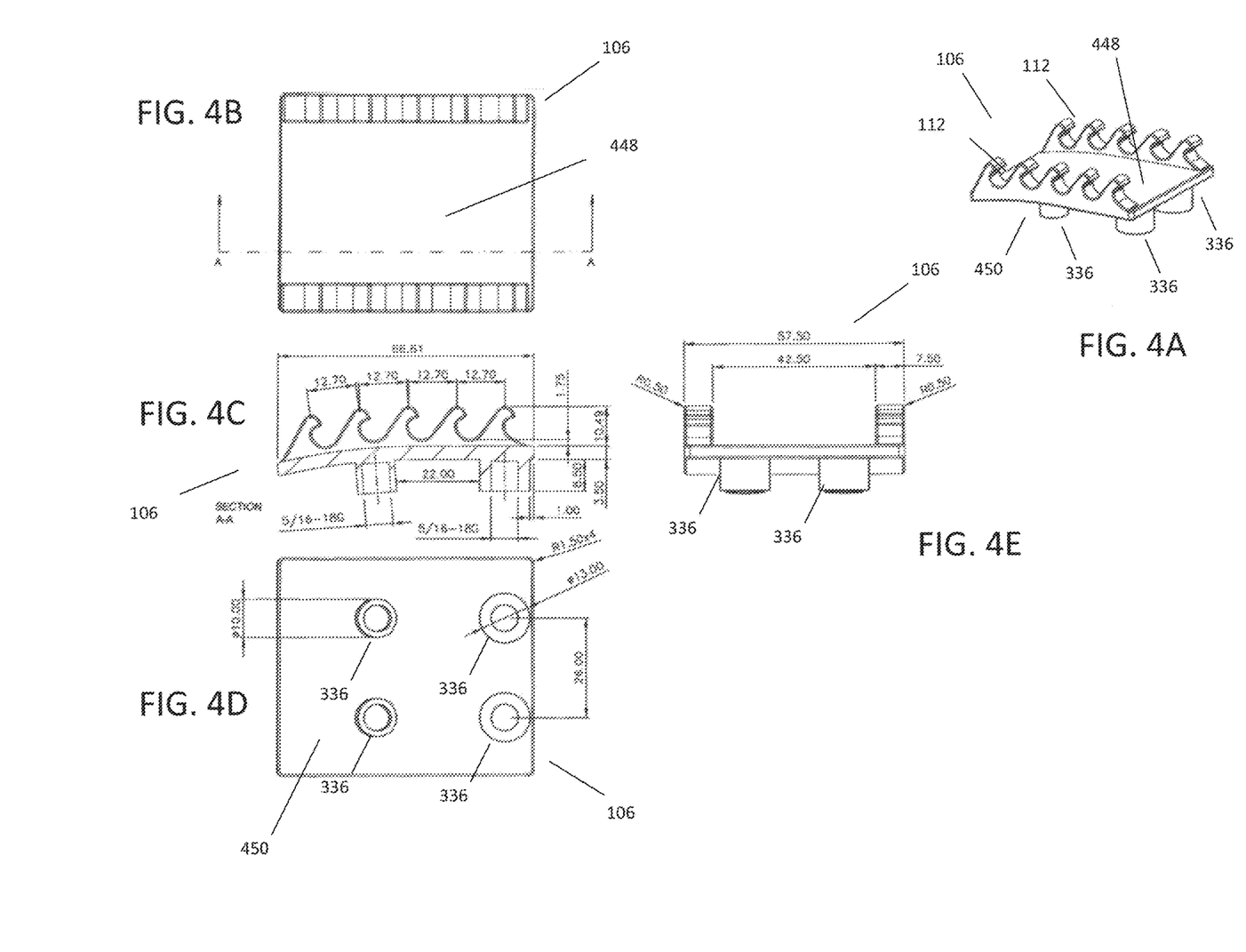
FIG. 4A is a perspective view of the anchor assembly from FIGS. 1A to 1C.
FIG. 4B is a front view of the anchor assembly from FIGS. 1A to 1C.
FIG. 4C is a cross-sectional side view of the anchor assembly from FIGS. 1A to 1C.
FIG. 4D is a rear view of the anchor assembly from FIGS. 1A to 1C.
FIG. 4E is an end view of the anchor assembly from FIGS. 1A to 1C.
Figure 5A:
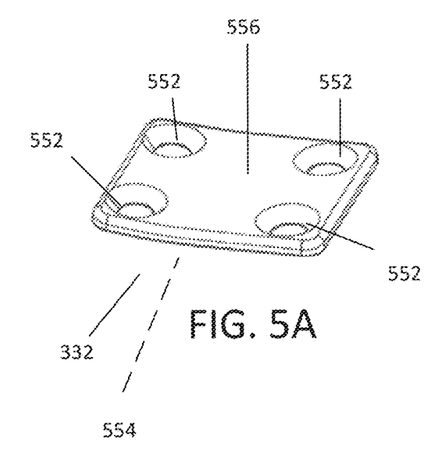
FIG. 5A is a perspective view of a back plate for the anchor assembly from FIGS. 1A to 1C.
Figure 5B:
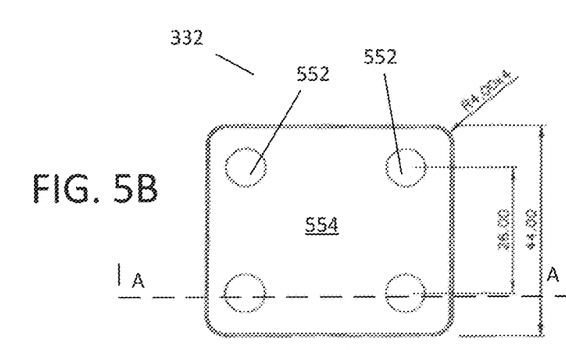
FIG. 5B is a front view of the back plate for the anchor assembly from FIGS. 1A to 1C.
Figure 5C:
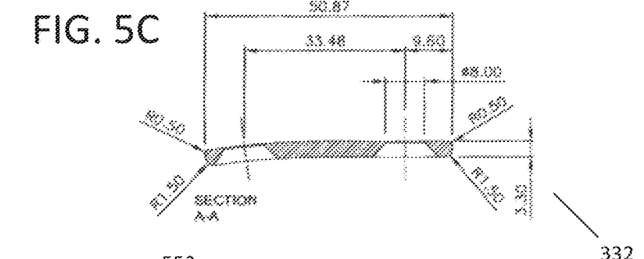
FIG. 5C is a cross-sectional side view of the back plate for the anchor assembly from FIGS. 1A to 1C.
Figure 5D:
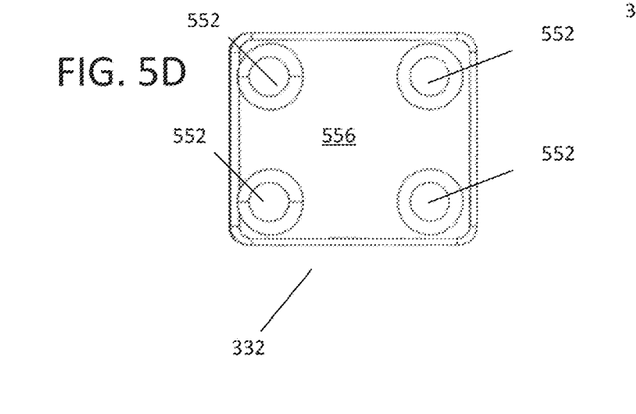
FIG. 5D is a rear view of the back plate for the anchor assembly from FIGS. 1A to 1C.
Figure 5E:
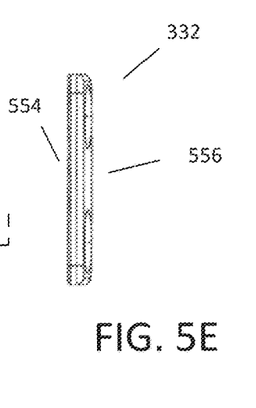
FIG. 5E is an end view of the back plate for the anchor assembly from FIGS. 1A to 1C.
Figures 6A, 6B:
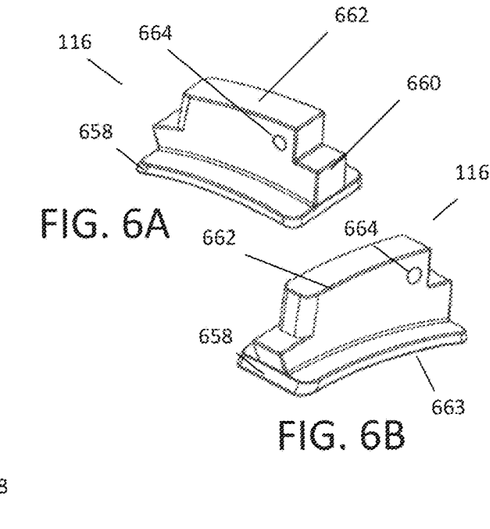
FIGS. 6A and 6B are perspective views of a support beam from FIGS. 1A to 1C.
Figure 6C:
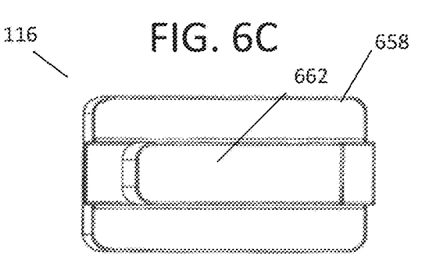
FIG. 6C is a front view of the support beam from FIGS. 1A to 1C.
Figures 6D, 6E, 6F, 6G:
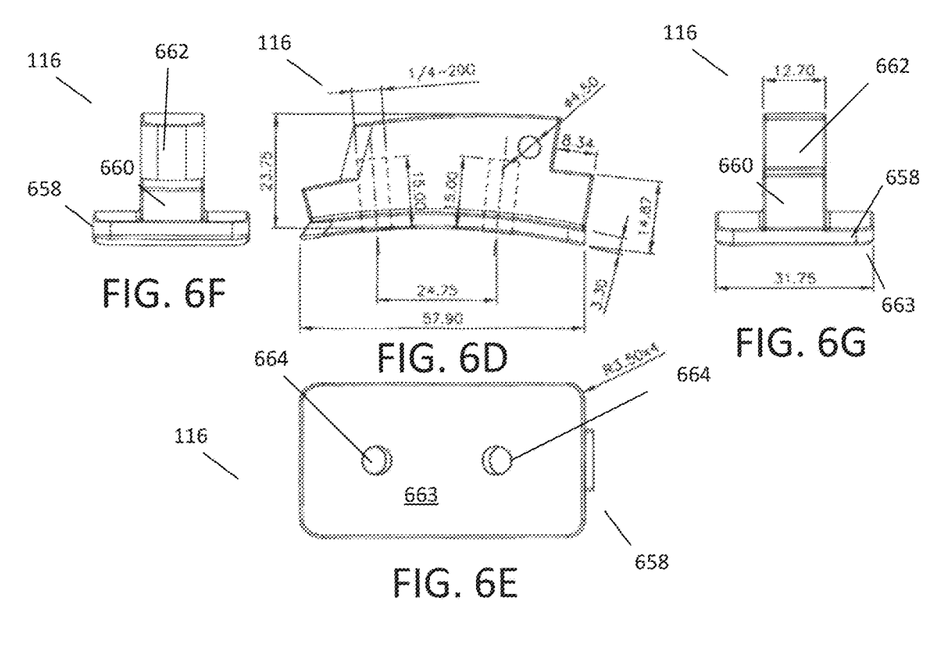
FIG. 6D is a cross-sectional side view of the support beam from FIGS. 1A to 1C.
FIG. 6E is a rear view of the support beam from FIGS. 1A to 1C.
FIGS. 6F and 6G are opposite end views of the anchor assembly from FIGS. 1A to 1C.
Figure 7A:
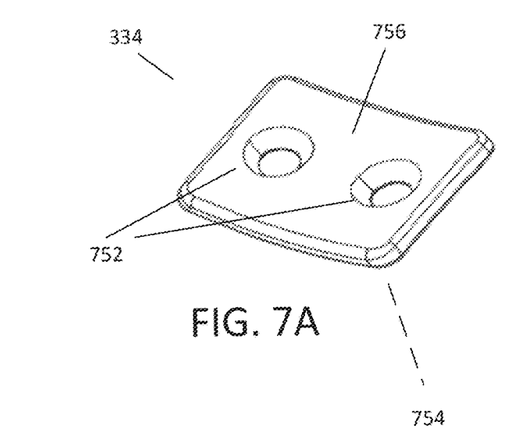
FIG. 7A is a perspective view of a back plate for the support beam from FIGS. 1A to 1C.
Figure 7B:
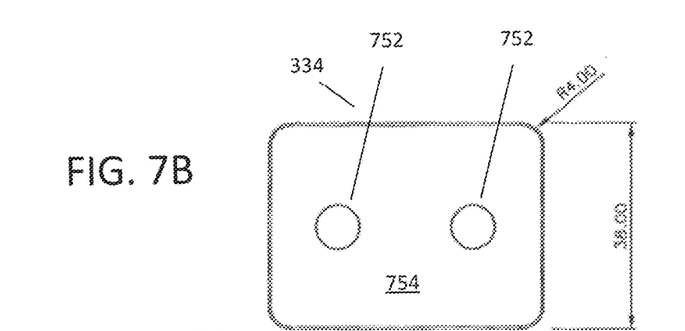
FIG. 7B is a front view of the back plate for the support beam from FIGS. 1A to 1C.
Figure 7C:
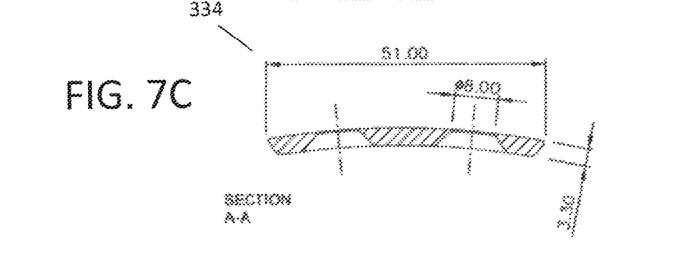
FIG. 7C is a cross-sectional side view of the back plate for the support beam from FIGS. 1A to 1C.
Figure 7D:
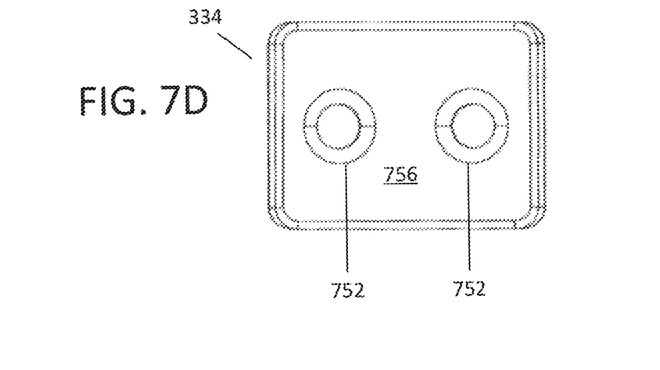
FIG. 7D is a rear view of the back plate for the support beam from FIGS. 1A to 1C.
Figure 8A:
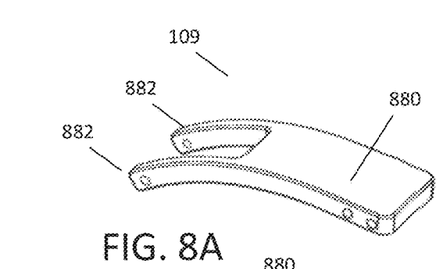
FIGS. 8A and 8B are perspective views of a hook portion from FIGS. 1A to 1C.
Figures 8B, 8G:
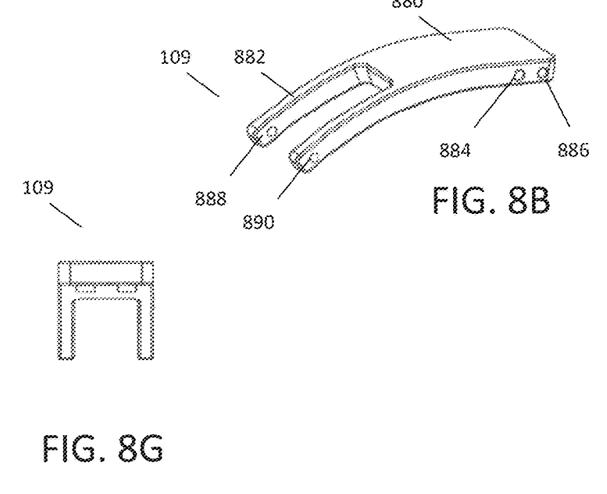
FIGS. 8F and 8G are opposite end views of the hook portion from FIGS. 1A to 1C.
Figure 8C:
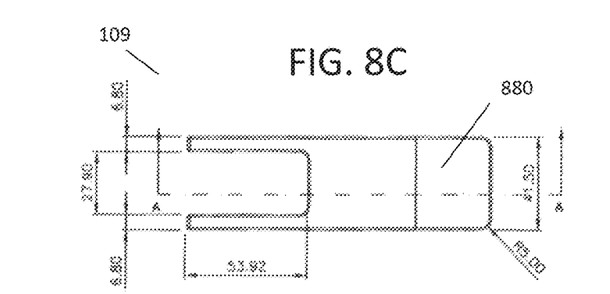
FIG. 8C is a front view of the hook portion from FIGS. 1A to 1C.
Figures 8D, 8E, 8F:
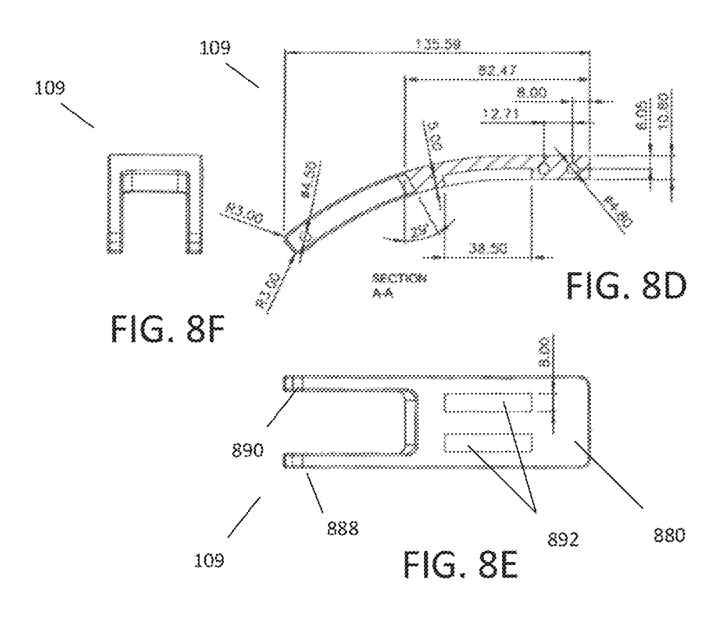
FIG. 8D is a cross-sectional side view of the hook portion from FIGS. 1A to 1C.
FIG. 8E is a rear view of the hook portion from FIGS. 1A to 1C.
Figure 9A:
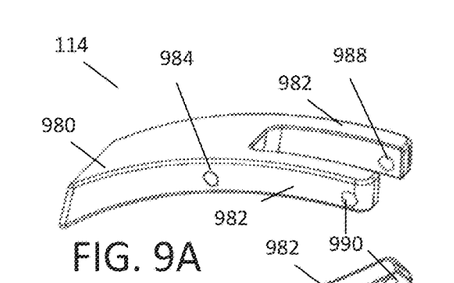
FIGS. 9A and 9B are perspective views of a lever mechanism from FIGS. 1A to 1C.
Figures 9B, 9E:
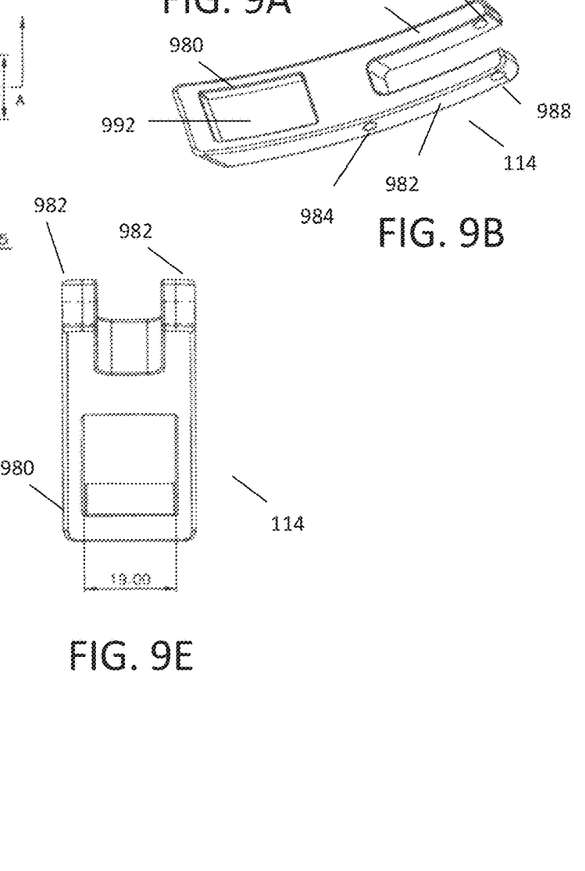
FIG. 9E is a rear view of the lever mechanism from FIGS. 1A to 1C.
Figure 9C:
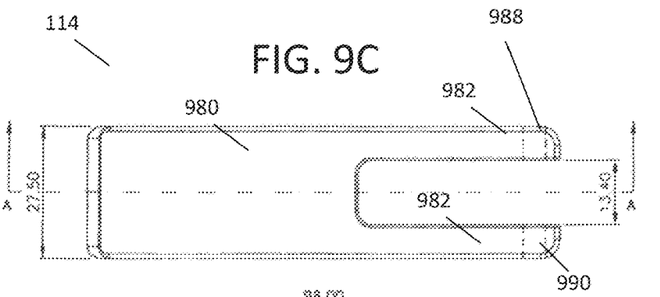
FIG. 9C is a front view of the lever mechanism from FIGS. 1A to 1C.
Figure 9D:
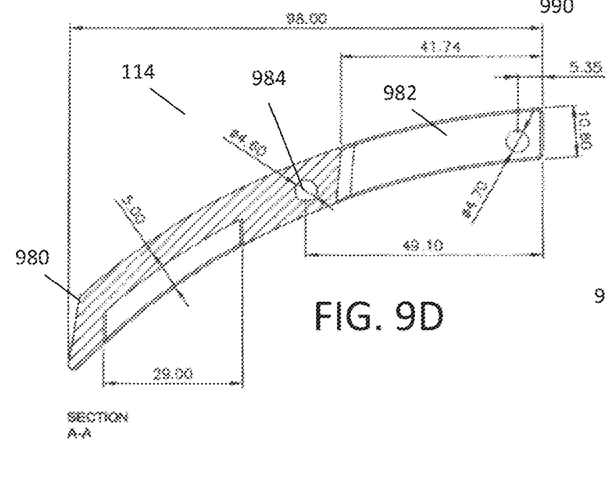
FIG. 9D is a cross-sectional side view of the lever mechanism from FIGS. 1A to 1C.
Figure 9F:
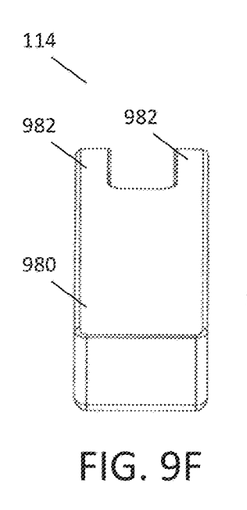
FIG. 9F is an end view of the lever mechanism from FIGS. 1A to 1C.

FIG. 2 is a view showing a first major surface (e.g., the back surface 218) of the strap portion 102 of the weightlifting belt of FIG. 1. A second major surface (e.g., the front surface 221 of the strap portion 102), which cannot be seen in FIG. 2, is opposite the back surface 218.

The strap portion 102 of the weightlifting belt in the illustrated implementation has four corners 219, a first longitudinal end 220, a second longitudinal end 222, a first lateral side 224, and a second lateral side 226. The strap portion 102 has a width (W) that can be measured from the first lateral side 224 to the second lateral side 226 and a length (L) that can be measured from the first longitudinal end 220 to the second longitudinal end 222. As FIG. 2 makes clear, the length (L) is significantly larger than the width (W). For example, typically, the length (L) is at least 24 inches and the width (W) is no more than 6 inches. More typically, the length (L) is between 75 centimeters (about 29.5 inches) and 135 centimeters (about 53 inches) and the width (W) is between 2.5 inches and 6 inches (e.g., either 2.5 inches, 3 inches, 4 inches, 5 inches, or 6 inches). Each of these dimensional ranges can vary of course. However, typically, the length (L) is significantly greater (e.g., at least 9 times longer) than the width (W) at any point along the length of belt regardless of whether the width varies or is uniform.

The sides and ends 220, 222, 224, 226 in the illustrated implementation are straight. Moreover, in the illustrated implementation, the first lateral side 224 is and parallel (and equidistant) to the second lateral side 226 along the entire length (L) of the strap portion 102 from the first longitudinal end 220 to the second longitudinal end 222. Likewise, in the illustrated implementation, the first longitudinal end 220 is parallel (and equidistant) to the second longitudinal end 222 along the entire width (W) of the strap portion 102 from the first lateral side 224 to the second lateral side 226.

Each corner 219 in the illustrated implementation is a slightly rounded 90-degree corner.

The thickness of the strap portion 102 (i.e., the distance from back surface 218 to the front surface 221) is typically uniform across an entirety of the strap portion 102. In a typical implementation, the thickness is between 10 millimeters and 13 millimeters. In general, thinner belts (e.g., ones having a thickness of 10 millimeters) may fit most body sizes and ability level, may be more comfortable, and may be easier to break-in and wear frequently than a 13-millimeter belt. Thicker belts (e.g., ones having a thickness of 13 millimeters) may provide superior support under heavier loads, especially while squatting. The thickness in various implementations, of course, can vary as well (e.g., from 8 millimeters to 15 millimeters).

There are two sets of holes in the illustrated strap portion 102.

The first set of holes 228 has four holes arranged in a pattern that approximates a rectangle that is approximately centered between the two lateral sides 224 and 226 of the strap portion 102 and is longitudinally displaced from the first end 220 of the strap portion 102 by just a short distance (less than three or four inches).

The four holes in the first set of holes 228 are configured to receive four cylindrical projections that extend from a back surface of the anchor assembly 106. The two holes that are closest to the first end 220 of the strap portion 102 are smaller in diameter than the two holes that are farther from the first end 220 of the strap portion 102. This is because the cylindrical projections intended to pass through the two holes that are closest to the first end 220 of the strap portion 102 have smaller outer diameters than the cylindrical projections intended to pass through the two holes that are farther from the first end 220 of the strap portion 102. In some implementations, the diameter of the two holes that are closest to the first end 220 of the strap is large enough to snugly accommodate a cylindrical projection that has a diameter of about 10 millimeters (e.g., 9.5 millimeters to 10.5 millimeters) and the diameter of the two holes that are farther from the first end 220 of the strap is large enough to snugly accommodate a cylindrical projection that has a diameter of 13 millimeters (e.g., 12.5 millimeters to 13.5 millimeters).

The second set of holes 230 has nine holes arranged in a linear pattern approximately midway between the lateral sides 224, 226 of the strap portion near the second end 222 of the strap portion 102. The second set of holes 230 starts at least an inch (typically at least 2-3 inches) from the second end 222 of the strap portion 102 and the holes are equally spaced. In some implementations, the holes may be spaced from one another so that the center of each hole is approximately 24.75 millimeters (e.g., 24.25 millimeters to 25.25 millimeters) from the center of each adjacent hole. Adjacent pairs of holes in the second set of holes 230 are configured to receive two cylindrical fastening elements (e.g., bolts) used to secure the lever-actuated hook assembly 108 in place.

The strap portion 102 of the weightlifting belt can be made from a variety of different base materials or combinations of materials. Some examples include leather, suede, nylon, or other fabric materials.

FIGS. 3A to 3D show different views of component parts of fastening assembly 104 from FIG. 1A to 1C. More specifically, the illustrated component parts include the anchor assembly 106 and the lever-actuated hook assembly 108. The strap portion 102 of the weightlifting belt 100 that appears in FIGS. 1A to 1C is not shown in FIGS. 3A to 3D.

The lever-actuated hook assembly 108 in the illustrated implementation is fully engaged to the anchor assembly 106 and the lever mechanism 114 is in a closed position. More specifically, the pins 110 (which are only shown in FIGS. 3A and 3B) of the lever-actuated hook assembly 108 are engaged in the tightest two notches 112 on the anchor assembly 106, and the lever mechanism 114 extends from the support beam 116 away from the anchor assembly 106. With the anchor assembly 106 and the lever-actuated hook assembly 108 so configured, they collectively form a slightly curved path (that approximates the curve of a person's mid-section where the belt would be worn). Moreover, the outward-facing surfaces of the lever-actuated hook assembly 108 in particular presents a relatively-smooth, aesthetically-pleasing curved appearance.

The illustrated fastening assembly 104 has a pair of back plates 332, 334 that sit against the back surface 218 of the strap portion 102 of the belt 100 and are used to facilitate securing the anchor assembly 106 and the lever-actuated hook assembly 108, respectively, to the strap portion 102 of the belt 100.

In this regard, the first back plate 332 has holes (not shown in FIGS. 3A to 3D) that accommodate fasteners (e.g., bolts or the like, also not shown in FIGS. 3A to 3D) that can pass through those holes and into threaded bores in the cylindrical projections 336 that are exposed at the back surface of the anchor assembly 106. In a typical implementation, the first back plate 332 has four holes arranged in a substantially rectangular pattern, which match up with four cylindrical projection 336 on the back surface of the anchor assembly 106. In a typical implementation, the cylindrical projections 336 extend back through the holes 228 in the strap portion 102 of the belt 100 and contact the first back plate 332 (see, e.g., FIGS. 3A to 3D). A fastening device (e.g., bolt, etc.) is screwed into the threaded bore of each cylindrical projection 336 to effectively secure the anchor assembly 106 to the first back plate 332.

The second back plate 334 also has holes 337 that accommodate fasteners 338 (e.g., bolts or the like, also not shown in FIGS. 3A to 3D) that can pass through those holes 337 and into threaded cylindrical bores exposed at the back surface of the support beam 116. In a typical implementation, the second back plate 334 has two holes arranged in a linear pattern (as shown) and match up with two threaded cylindrical bores 340 on the back surface of the support beam 116. In a typical implementation, one of the fasteners 338 extends through each hole 337 in the second back plate 334, through one of the holes 230 in the strap portion 102 of the weightlifting belt 100 and is screwed into a corresponding one of the threaded cylindrical bores 340 in the support beam 116 to effectively secure the lever-actuated hook assembly to the second back plate 334.

FIGS. 3A to 3D also shows two pins 342, 344 that define lateral pivot axes for the lever-actuated hook assembly 108. More specifically, a first lateral pin 342 extends laterally through a hole in the support beam 116 and into the lever mechanism 114 on opposite sides of the support beam 116. The lever mechanism 114 is coupled to the first lateral pin 342 in a manner that enables the lever mechanism to pivot about a pivot axis defined by the first lateral pin 342 between a loose position (see, e.g., FIG. 1B) and a tightened position (see, e.g., FIG. 1C). The first lateral pin 342 is located on the support beam 116 near an end of the support beam 116 that is closest to the second longitudinal end 222 of the strap portion 102 of the belt 100. The A second lateral pin 344 extends laterally through the lever mechanism 114 at an approximate longitudinal midpoint of the lever mechanism 114 and into the hook portion 109 of the lever actuated hook assembly 108. The lever mechanism 114 and the hook portion 109 of the lever actuated hook assembly 108 are coupled to the second lateral pin 344 in a manner that enables both to pivot relative to one another about a lateral axis defined by the second lateral pin 344. More specifically, this relative pivot motion enables the lever mechanism 114 and the hook portion 109 to change their configuration relative to one another between their configurations in FIG. 1B and the configurations in FIG. 1C.

FIGS. 4A-9F are views of individual components of the fastening assembly 104 from FIGS. 1A to 3D. Some of these drawings provide numerical dimensions, which are in millimeters, unless otherwise indicated. Any dimensions provided should be considered as having a tolerance of +/−0.5 millimeters (if in millimeters), +/−0.15 inches (if in inches), and +/−1 degree (for angles). Of course, any dimensions (or tolerances) provided are exemplary only and should not limit the scope of any claimed subject matter unless expressly stated in a claim and, then, only the claim with that express statement should be so limited (to the stated dimension and/or tolerance and its equivalents).

FIGS. 4A to 4E show views of the anchor assembly 106. The anchor assembly 106 in the illustrated implementation is a rigid structure that includes a slightly curved plate portion 446. The slightly curved plate portion 446 has a substantially rectangular outline when viewed from above. (See, e.g., FIG. 4B). The plate portion 446 has a front surface 448 and a back surface 450. Two rows of notches 112 extend up from the front surface 448 of the plate portion 446 at opposite lateral edges thereof. Each notch 112 is defined as a space adjacent to a structure having a wave-like shape. The notches 112 on each lateral side of the front surface 448 are aligned with the notches 112 on the other lateral side of the front surface 448. There is an empty space on the front surface 448 between the two rows of notches 112. This space is sized to accommodate the width of the hook portion 109 of the lever-actuated hook assembly 108 for when the hook portion 109 of the lever-actuated hook assembly 108 is positioned as shown in FIG. 1B or 1C, for example.

The four cylindrical projections 336 extend out from the back surface 450 of the plate portion 446. Each cylindrical projection 336 defines an internal bore that may be threaded. The four cylindrical projections 336 are arranged in a substantially rectangular pattern (e.g., such that the center of each bore would be positioned at a corner of the rectangle). The rectangular pattern is offset from back surface 450 of the plate portion so that two of the cylindrical projections 336 are much closer to an edge of the back surface 450 than the other two cylindrical projections 336. Although all four cylindrical projections have the same inner bore size, the wall (and, therefore, the outer diameter) of the two cylindrical projections 336 that are closest to the edge of the back surface 450 are larger than the wall (and, therefore, the outer diameter) of the other cylindrical projections 336.

FIGS. 5A to 5E show views of the first back plate 332 (used to mount the anchor assembly 106). The first back plate 332 in the illustrated implementation is a rigid structure that is thin, slightly curved, and has a substantially rectangular outline (with rounded corners) when viewed from above. (See, e.g., FIG. 5B). The first back plate 332 has a front surface 554 and a back surface 556. There are four openings 552 in the first back plate 332 that extend through the first back plate 332 between the front surface 554 and the back surface 556. The openings 552 are equally-sized and configured in a substantially rectangular configuration, with one opening near each of the four corners of the plate 332. Each opening 522 is countersunk from its back surface 556.

FIGS. 6A-6G show views of the support beam 116. The support beam 116 in the illustrated implementation is a rigid structure that has a back surface 663 (that sits against the strap portion 102 of the belt 100 when the belt 100 is assembled). The back surface 663 is smooth and slightly curved from end-to-end and is smooth from side-to-side, except for two holes 664 that extend into the back surface 663. The holes 664 in the illustrated implementation are arranged along a longitudinal axis about midway between the sides of the back surface 663. A back surface 663 is part of a lower portion 658 of the support beam 116 that is thin, slightly curved, and has a substantially rectangular outline (with rounded corners) when viewed from above. (See, e.g., FIG. 6C). A projection extends from a front surface of the lower portion 658 of the support beam 116. This projection has a longer lower section 660 and a shorter upper section 662. The longer lower section 660 of the projection extends across the front surface of the lower portion 658 of the support beam 116 and spans an entirety of that surface from end-to-end in a longitudinal direction about halfway between lateral sides of the thin lower portion 658. The shorter upper section 662 of the projection has the same lateral width as the longer lower section 660 and follows the same longitudinal path as the longer lower section 660, it is just shorter (and has a slightly different overall shape) than the longer lower section 660 of the projection. A hole 664 extends laterally through one end of the upper section 662 of the projection. The hole 664 is sized to receive a shaft that will define an axis around which the lever mechanism 114 will be able to swing. The upper section of the projection is sized and shaped to snugly fit within a frame defined by the lever mechanism 114 when the lever mechanism 114 is in a closed and tightened configuration (e.g., as shown in FIG. 1C).

FIGS. 7A to 7D show views of the second back plate 334 (used to mount the support beam 116). The second back plate 334 in the illustrated implementation is a rigid structure that is thin, slightly curved, and has a substantially rectangular outline (with rounded corners) when viewed from above. (See, e.g., FIG. 7B). The second back plate 334 has a front surface 754 and a back surface 756. There are two openings 752 in the first back plate 332 that extend through the first back plate 332 between the front surface 554 and the back surface 556. The openings 552 are equally-sized and configured in a substantially rectangular configuration, with one opening near each of the four corners of the plate 332. Each opening 522 is countersunk from its back surface 556.

FIGS. 8A to 8G show views of the hook portion 109. The hook portion 109 in the illustrated implementation is a rigid structure that is thin, slightly curved, with a main body portion 880 and two substantially parallel prongs 882 that extend from an end of the main body portion 880. Lateral holes 884, 886 are provided through the main body portion 880 near an end of the main body portion 880 opposite the prongs 882. Each of these holes 884, 886 is sized to receive a pin (not shown on FIGS. 8A to 8G but see 110 in FIG. 1A) that can engage one of the notches 112 on the anchor assembly 108. There are other holes 888, 890 that extend laterally through the distal ends of the prongs 882. These holes are sized and shaped to receive a shaft that will define an axis about which the hook portion 109 can rotate relative to the lever mechanism 114. There are two indentations 892 formed in a back surface of the hook portion 109. These indentations 892, which can take any one of a variety of forms, simply reduce the weight and cost of the hook portion 109.

FIGS. 9A to 9F show views of the lever mechanism 114. The lever mechanism 114 in the illustrated implementation is a rigid structure that is thin, slightly curved, with a main body portion 980 and two substantially parallel prongs 982 that extend from an end of the main body portion 980. A hole 984 extends laterally through the main body portion 980 near the prongs 982. The hole 984 is sized to receive a shaft that will pass through the hole and through the holes 888, 890 in the hook portion 109. The shaft will define an axis about which the lever mechanism 114 and the hook portion 109 can rotate relative to one another. There are other holes 988, 990 that extend laterally through the distal ends of the prongs 882. These holes 988, 990 are sized and shaped to receive a shaft that will pass into the holes 988, 990 and through hole 664 in the support beam 116 and define an axis about which the lever mechanism 114 can rotate relative to the support beam 116. There is an indentation 992 formed in a back surface of the lever mechanism 114. These indentations 992, which can take any one of a variety of forms, simply reduce the weight and cost of the lever mechanism 114.

A number of embodiments of the invention have been described. Nevertheless, it will be understood that various modifications may be made without departing from the spirit and scope of the invention.

The strap portion can be varied in a number of ways. For example, the length and width can be varied. The material of the strap portion can be varied. The number and relative arrangement of holes at either end of the strap portion can vary. Moreover, the first lateral side surface 224 of the strap portion 102 need not be parallel (and equidistant) to the second lateral side surface 226 along the entire length of the strap portion 102 from the first longitudinal end 220 to the second longitudinal end 222. Instead, in some implementations, the first lateral side surface 224 and/or the second lateral side surface 226 may be contoured to define a wider portion and one or more narrower portions. In a typical implementation, the wider portion might be located somewhere in the middle of the strap portion (i.e., longitudinally displaced from both longitudinal ends 220, 222) with the narrower portions being located at both longitudinal ends of the strap portion 102. Thus, when a user wears the belt, the narrower portions (and, of course, the fastening assembly 104) will be in front of the user, while the wider portion is located at least on the user's back.

The anchor assembly can be varied in a number of ways. For example, the length and the width of the anchor assembly can be varied. The size and shape of the structure that defines the notches can be varied. The size, shape and relative configuration of mounting holes at the back surface of the anchor assembly can be varied. The anchor assembly (and any other rigid components) can be made from a variety of different rigid materials or combinations of materials (e.g., steel, etc.). The back plates can be varied (e.g., by size, number and location of holes, etc.). The size and shape of the support beam (including the size, shape and relative configuration of its mounting holes), the lever mechanism, and the hook assembly can be varied.

According to some implementations disclosed herein, the wearer of the weightlifting belt will have the ability to choose a tightness setting across a 2-inch range with 0.5-inch increments simply by adjusting which notches on the anchor assembly the pins engage. In various implementations, the 2-inch range and/or the 0.5-inch increment dimension can vary (e.g., by changing the number, size or configuration of the notches and pins).

Moreover, according to some implementations disclosed herein, the support beam location on the belt can be varied up to 9-inches with some incremental dimension. These, too, can be varied, up or down, by modifying the support beam, the back plate, and/or the holes in the strap portion.

The bottom of the main beam (116) may be extended to increase the surface area of the pivot point.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Other implementations are within the scope of the claims.

What is claimed is:

1. A weightlifting belt comprising:
   a flexible strap portion that comprises a first major surface, a second major surface opposite the first major surface, a first longitudinal end, a second longitudinal end, a first lateral side, and a second lateral side, wherein the flexible strap portion defines a first set of holes near the first longitudinal end of the flexible strap portion and a second set of holes near the second longitudinal end of the flexible strap portion;
   an anchor assembly attached to the flexible strap portion and in contact with the second major surface of the flexible strap portion near the first longitudinal end of the flexible strap portion, wherein the anchor assembly defines a plurality of notches arranged in one or more rows that extend longitudinally along an outwardly-facing surface of the anchor assembly, wherein the anchor assembly comprises anchor projections that extend from a back of the anchor assembly and that pass through holes of the first set of holes in the flexible strap portion; and
   a lever-actuated hook assembly attached to the flexible strap portion and in contact with the second major surface of the flexible strap portion near the second longitudinal end of the flexible strap portion, wherein the lever-actuated hook assembly comprises a support beam mounted to and in direct physical contact with the flexible strap portion, a lever mechanism connected to and in direct physical contact with the support beam, and a hook portion connected to and in direct physical contact with the lever mechanism, and pins that extend in a laterally-outward direction from a distal end of the hook portion of the lever-actuated hook assembly,
   a pair of back plates that sits against the first major surface of the flexible strap portion and facilitate securing the anchor assembly and the lever-actuated hook assembly, respectively, to the flexible strap portion,
   wherein the lever-actuated hook assembly is configured to engage the anchor assembly so as to hold the first longitudinal end of the strap portion close to, or in physical contact with, the second longitudinal end of the strap portion so as to form a loop that can fit around a waist of a human.

2. The weightlifting belt of claim 1, wherein the pins are configured to engage one or more of the notches on the anchor assembly to hold the first longitudinal end of the strap portion close to, or in physical contact with, the second longitudinal end of the strap portion so as to form a loop that can fit around a waist of a human.

3. The weightlifting belt of claim 2, wherein the pair of back plates comprises:
   a first back plate in contact with the first major surface of the strap portion near the first longitudinal end of the flexible strap portion, and
   a second back plate in contact with the first major surface of the strap portion near the second longitudinal end of the flexible strap portion.

4. The weightlifting belt of claim 3, wherein the anchor assembly is mounted to the first back plate via one of more fastening devices that pass through one or more corresponding holes in the strap portion near the first longitudinal end of the strap portion to secure the anchor assembly to the first back plate, and
   wherein the lever-actuated hook assembly is mounted to the second back plate via one or more fastening devices that pass through one or more corresponding holes in the strap portion near the second longitudinal end of the strap portion to secure the lever-actuated hook assembly to the second back plate.

5. The weightlifting belt of claim 4, wherein the lever-actuated hook assembly comprises:
   a support beam, with one or more openings in a back surface thereof to receive the one more fasteners that pass through the one or more corresponding holes in the strap portion near the second longitudinal end of the strap portion;
   a lever mechanism coupled to the support beam via a shaft that passes through the lever mechanism and support beam in a manner that enables the lever mechanism to pivot about an axis defined by the shaft relative to the support beam; and
   a hook portion coupled to the lever mechanism via a shaft that passes through the hook portion and the lever mechanism in a manner that enables the hook portion to pivot about an axis defined by the shaft relative to the lever mechanism.

6. The weightlifting belt of claim 5, wherein the hook portion comprises the one or more pins and wherein each of the one or more pins extends in a lateral direction from a main body portion of the hook portion of the lever-actuated hook assembly.

7. The weightlifting belt of claim 6, wherein the notches are arranged on the anchor assembly in two longitudinal rows with a space therebetween that receives a main body portion of the hook assembly when the one or more pins on the hook portion engage the notches on the anchor assembly.

8. The weightlifting belt of claim 6, configured such that the lever mechanism and the hook portion can be extended in a substantially longitudinal direction from the support beam to facilitate engaging the one or more pins into the plurality of grooves, and then the lever mechanism can be pivoted to tighten the belt.

9. The weightlifting belt of claim 5, wherein one or more of the pins extends in a laterally outward first direction from the main body portion of the lever-actuated hook assembly, and wherein one or more of the pins extends in a laterally outward second direction from the main body portion of the lever-actuated hook assembly.

10. The weightlifting belt of claim 5, wherein each of the lever mechanism and the hook portion of the lever-actuated hook assembly is curved,
    wherein the weightlifting belt is configured such that the lever mechanism and the hook portion curve in opposite directions when the level-actuated hook assembly is in an extended configuration, and wherein the lever mechanism and the hook portion curve in a common direction when the level-actuated hook assembly is in a closed configuration.

11. The weightlifting belt of claim 10, wherein the lever mechanism of the lever-actuated hook assembly comprises a surface with edges, wherein an entirety of the outwardly-facing surface of the lever mechanism, between and to every one of the edges, is smooth, and
    wherein the hook portion of the lever-actuated hook assembly comprises edges and an outwardly-facing surface that extends between and to every one of the edges of the hook portion, wherein an entirety of the outwardly-facing surface of the hook portion, to every one of the edges, is smooth.

12. The weightlifting belt of claim 11, wherein the support beam of the lever-actuated assembly comprises edges and an outwardly-facing surface that extends between and to every one of the edges of the support beam, wherein an entirety of the outwardly-facing surface of the support beam, to every one of the edges of the support beam, is smooth.

13. The weightlifting belt of claim 12, wherein the smooth outwardly facing surface of the lever mechanism, the smooth outwardly facing surface of the hook portion, and the smooth outwardly facing surface of the support beam align with one another to collectively present a smooth, curved appearance, when the lever-actuated hook assembly is engaged to the anchor assembly and the lever actuated hook mechanism is in a closed position.

14. The weightlifting belt of claim 1, wherein the strap portion of the belt has a length that extends from the first longitudinal end to the second longitudinal end, and a width that extends from the first lateral side to the second lateral side,
    wherein the length is significantly greater than the width at every point along the length of belt regardless of whether the width varies or is uniform.

15. The weightlifting belt of claim 14, wherein the length is at least nine times greater than the width at any point along the length.

16. The weightlifting belt of claim 1, wherein the strap portion of the belt has a uniform thickness between 8 millimeters and 15 millimeters.

17. The weightlifting belt of claim 4, wherein the first back plate and the second back plate are configured to not overlap with one another when the weightlifting belt is configured in a closed and tightened configuration.

18. The weightlifting belt of claim 1, wherein the second set of holes comprises a plurality of holes arranged in a linear pattern to accommodate different lengthwise positioning of the support beam portion of the lever-actuated hook mechanism on the flexible strap portion.

19. A method comprising:
placing a weightlifting belt around a waist of a person, the weightlifting belt comprising:
    a flexible strap portion that comprises a first major surface, a second major surface opposite the first major surface, a first longitudinal end, a second longitudinal end, a first lateral side, and a second lateral side, wherein the flexible strap portion defines a first set of holes near the first longitudinal end of the flexible strap portion and a second set of holes near the second longitudinal end of the flexible strap portion;
    an anchor assembly attached to the flexible strap portion and in contact with the second major surface of the flexible strap portion near the first longitudinal end of the flexible strap portion, wherein the anchor assembly defines a plurality of notches arranged in one or more rows that extend longitudinally along an outwardly-facing surface of the anchor assembly, wherein the anchor assembly comprises anchor projections that extend from a back of the anchor assembly and that pass through holes of the first set of holes in the flexible strap portion;
    a lever-actuated hook assembly attached to the flexible strap portion and in contact with the second major surface of the flexible strap portion near the second longitudinal end of the flexible strap portion, wherein the lever-actuated hook assembly comprises a support beam mounted to and in direct physical contact with the flexible strap portion, a lever mechanism connected to and in direct physical contact with the support beam, and a hook portion connected to and in direct physical contact with the lever mechanism, and pins that extend in a laterally-outward direction from a distal end of the hook portion of the lever-actuated hook assembly, and
    a pair of back plates that sits against the first major surface of the flexible strap portion and facilitate securing the anchor assembly and the lever-actuated hook assembly, respectively, to the flexible strap portion,
    wherein the lever-actuated hook assembly is configured to engage the anchor assembly so as to hold the first longitudinal end of the strap portion close to, or in physical contact with, the second longitudinal end of the strap portion so as to form a loop that can fit around the waist of the person, and fastening the weightlifting belt on the waist.

20. The method of claim 19,
    wherein each of the pins is configured to engage a corresponding one of the notches on the anchor assembly,
    wherein fastening the weightlifting belt on the waist comprises:
        engaging one or more of the pins into a corresponding one or more of the notches to hold the first longitudinal end of the strap portion close to, or in physical contact with, the second longitudinal end of the strap portion so as to form a loop that fits around the person's waist; and
        tightening the weightlifting belt around the person's waist.

21. The method of claim 20, wherein the weightlifting belt further comprises:
    a first back plate in contact with the first major surface of the strap portion near the first longitudinal end of the flexible strap portion, and a second back plate in contact with the first major surface of the strap portion near the second longitudinal end of the flexible strap portion,
- wherein the anchor assembly is mounted to the first back plate via one of more fastening devices that pass through one or more corresponding holes in the strap portion near the first longitudinal end of the strap portion to secure the anchor assembly to the first back plate, and
- wherein the lever-actuated hook assembly is mounted to the second back plate via one or more fastening devices that pass through one or more corresponding holes in the strap portion near the second longitudinal end of the strap portion to secure the lever-actuated hook assembly to the second back plate, wherein tightening the weightlifting belt comprises:
- operating the lever-actuated hook assembly to pull the first longitudinal end of the strap portion closer to the second longitudinal end of the strap portion thereby tightening the weightlifting belt around the person's waist.

22. The method of claim 21, wherein the lever-actuated hook assembly comprises:
- a support beam, with one or more openings in a back surface thereof to receive the one more fasteners that pass through the one or more corresponding holes in the strap portion near the second longitudinal end of the strap portion;
- a lever mechanism coupled to the support beam via a shaft that passes through the lever mechanism and support beam in a manner that enables the lever mechanism to pivot about a first axis defined by the shaft relative to the support beam; and
- a hook portion coupled to the lever mechanism via a shaft that passes through the hook portion and the lever mechanism in a manner that enables the hook portion to pivot about a second axis defined by the shaft relative to the lever mechanism, and wherein operating the lever-actuated hook assembly to pull the first longitudinal end of the strap portion closer to the second longitudinal end of the strap portion thereby tightening the weightlifting belt around the person's waist comprises:
- causing the lever mechanism to pivot about a first pivot axis relative to the support beam and to pivot about the second axis relative to the hook portion while one or more of the pins of the hook portion are engaged to the anchor assembly.

23. The method of claim 22, further comprising:
- performing a feat of strength, by the person, while wearing the belt.

24. The method of claim 23, wherein the feat of strength is a set of squats.

* * * * *